United States Patent
Canovas Vidal et al.

(10) Patent No.: US 11,819,401 B2
(45) Date of Patent: Nov. 21, 2023

(54) INTRAOCULAR LENSES WITH CUSTOMIZED ADD POWER

(71) Applicant: AMO Groningen B.V., Groningen (NL)

(72) Inventors: Carmen Canovas Vidal, Groningen (NL); Robert Rosén, Groningen (NL); Marrie Van Der Mooren, Engelbert (NL); Patricia A. Piers, Groningen (NL)

(73) Assignee: AMO Groningen B.V., Groningen (NL)

( * ) Notice: Subject to any disclaimer, the term of this patent is extended or adjusted under 35 U.S.C. 154(b) by 0 days.

(21) Appl. No.: 17/246,246

(22) Filed: Apr. 30, 2021

(65) Prior Publication Data

US 2021/0251743 A1 Aug. 19, 2021

Related U.S. Application Data

(62) Division of application No. 16/128,231, filed on Sep. 11, 2018, now Pat. No. 11,000,362.

(60) Provisional application No. 62/556,752, filed on Sep. 11, 2017.

(51) Int. Cl.
*A61F 2/16* (2006.01)
*G02C 7/04* (2006.01)
*G02C 7/02* (2006.01)

(52) U.S. Cl.
CPC .......... *A61F 2/1618* (2013.01); *A61F 2/1624* (2013.01); *A61F 2/1613* (2013.01); *A61F 2/1616* (2013.01); *A61F 2/1637* (2013.01); *A61F 2/1654* (2013.01); *A61F 2002/1681* (2013.01); *A61F 2240/002* (2013.01); *A61F 2250/0064* (2013.01); *G02C 7/027* (2013.01); *G02C 7/041* (2013.01)

(58) Field of Classification Search
CPC .... A61F 2/1613; A61F 2/1616; A61F 2/1618; A61F 2/1637; A61F 2/1654; A61F 2240/002; G02C 7/027
See application file for complete search history.

(56) References Cited

U.S. PATENT DOCUMENTS

| | | | |
|---|---|---|---|
| 4,710,193 A | 12/1987 | Volk | |
| 5,050,981 A | 9/1991 | Roffman | |
| 5,760,871 A | 6/1998 | Kosoburd et al. | |

(Continued)

FOREIGN PATENT DOCUMENTS

| | | |
|---|---|---|
| JP | 9196820 A | 7/1997 |
| WO | 02088830 A1 | 11/2002 |

(Continued)

OTHER PUBLICATIONS

Eibschitz-Tsimhoni M., et al., "Intraocular Lens Power Calculation in Children," Survey of Ophthalmology, 2007, vol. 52 (5), pp. 474-482.

(Continued)

*Primary Examiner* — Javier G Blanco
(74) *Attorney, Agent, or Firm* — Johnson & Johnson Surgical Vision, Inc.

(57) ABSTRACT

Intraocular lenses with a base optical power and a customized add power. The add power is customized based on at least one of ocular biometry of an individual, position of the intraocular lens in the eye and a preferred reading distance.

4 Claims, 5 Drawing Sheets

(56) References Cited

U.S. PATENT DOCUMENTS

| | | | |
|---|---|---|---|
| 5,777,719 | A | 7/1998 | Williams et al. |
| 5,968,095 | A | 10/1999 | Norrby |
| 6,050,687 | A | 4/2000 | Bille et al. |
| 6,095,651 | A | 8/2000 | Williams et al. |
| 6,224,211 | B1 | 5/2001 | Gordon |
| 6,338,559 | B1 | 1/2002 | Williams et al. |
| 6,413,276 | B1 | 7/2002 | Werblin |
| 6,499,843 | B1 | 12/2002 | Cox et al. |
| 6,652,098 | B2 | 11/2003 | Suzaki et al. |
| 6,663,240 | B2 | 12/2003 | Patel |
| 6,695,880 | B1 | 2/2004 | Roffman et al. |
| 6,786,603 | B2 | 9/2004 | Altmann |
| 6,808,265 | B2 | 10/2004 | Cox |
| 6,808,266 | B2 | 10/2004 | Youssefi |
| 6,817,714 | B2 | 11/2004 | Altmann |
| 6,830,712 | B1 | 12/2004 | Roffman et al. |
| 6,905,641 | B2 | 6/2005 | Platt et al. |
| 7,044,604 | B1 | 5/2006 | Arrowsmith |
| 7,281,795 | B2 | 10/2007 | Sandstedt et al. |
| 7,322,699 | B2 | 1/2008 | Barth et al. |
| 7,883,208 | B2 | 2/2011 | Norrby et al. |
| 10,159,565 | B2 | 12/2018 | Van et al. |
| 2003/0128336 | A1 | 7/2003 | Jethmalani et al. |
| 2004/0085515 | A1 | 5/2004 | Roffman et al. |
| 2004/0088050 | A1 | 5/2004 | Norrby et al. |
| 2004/0100619 | A1 | 5/2004 | Olivier et al. |
| 2004/0119174 | A1 | 6/2004 | Hofmann et al. |
| 2004/0156013 | A1 | 8/2004 | Lindacher et al. |
| 2004/0246440 | A1 | 12/2004 | Andino et al. |
| 2005/0007551 | A1 | 1/2005 | Wakil et al. |
| 2005/0056953 | A1 | 3/2005 | Hofmann et al. |
| 2005/0074616 | A1 | 4/2005 | Harchanko et al. |
| 2005/0104240 | A1 | 5/2005 | Jethmalani et al. |
| 2005/0105048 | A1 | 5/2005 | Warden et al. |
| 2005/0122472 | A1 | 6/2005 | Fisher et al. |
| 2005/0195361 | A1 | 9/2005 | Jethmalani et al. |
| 2005/0200809 | A1 | 9/2005 | Dreher et al. |
| 2006/0238702 | A1 | 10/2006 | Glick et al. |
| 2006/0274268 | A1 | 12/2006 | Andino et al. |
| 2007/0260157 | A1 | 11/2007 | Norrby |
| 2009/0281552 | A1 | 11/2009 | Hiramatsu et al. |
| 2010/0281021 | A1* | 11/2010 | Weeber ............ A61F 2/1618 707/E17.014 |
| 2011/0015541 | A1 | 1/2011 | Padrick et al. |
| 2012/0158132 | A1 | 6/2012 | Canovas et al. |
| 2012/0274895 | A1 | 11/2012 | Van Der Mooren et al. |
| 2014/0125955 | A1 | 5/2014 | Bissman et al. |
| 2015/0366656 | A1 | 12/2015 | Wortz et al. |
| 2017/0042665 | A1 | 2/2017 | Currie et al. |
| 2017/0213306 | A9 | 7/2017 | Weeber et al. |

FOREIGN PATENT DOCUMENTS

| | | | |
|---|---|---|---|
| WO | 03022137 | A2 | 3/2003 |
| WO | 03057022 | A1 | 7/2003 |
| WO | 03096927 | A2 | 11/2003 |
| WO | 04028356 | A1 | 4/2004 |
| WO | 04039554 | A2 | 5/2004 |
| WO | 04060643 | A1 | 7/2004 |
| WO | 04072709 | A1 | 8/2004 |
| WO | 2004096014 | A2 | 11/2004 |
| WO | 06053216 | A2 | 5/2006 |
| WO | 2009076670 | A1 | 6/2009 |
| WO | 2010035139 | A2 | 4/2010 |
| WO | 2011100544 | A1 | 8/2011 |
| WO | 2012082898 | A1 | 6/2012 |

OTHER PUBLICATIONS

Hill W.E., "Making Iol Power Calculation More Powerful," Eye World Magazine, 2003, pp. 1-4.

Holladay J.T., et al., "A Three-Part System for Refining Intraocular Lens Power Calculations," Journal of Cataract and Refractive Surgery, Jan. 1988, vol. 14 (1), pp. 17-24.

Norrby et al., "Reduction of trend errors in power calculation by linear transformation of measured axial lengths," J Cataract Refractive Surgery, pp. 100-105, 2003, vol. 29.

Norrby S., et al., "Clinical Application of the Lens Haptic Plane Concept with Transformed Axial Lengths," Journal of Cataract and Refractive Surgery, 2005, vol. 31 (7), pp. 1338-1344.

Norrby S., et al., "Comparison of 2 A-scans," Journal of Cataract and Refractive Surgery, 2003, vol. 29 (1), pp. 95-99.

Norrby S., et al., "Sources of Error in Intraocular Power Calculation," Journal of Cataract & Refractive Surgery, 2008, vol. 34 (3), pp. 368-376.

Norrby S., "Using the Lens Haptic Plane Concept and Thick-Lens Ray Tracing to Calculate Intraocular Lens Power," Journal of Cataract & Refractive Surgery, 2004, vol. 30 (5), pp. 1000-1005.

Norrby, "The Dubbelman eye model analysed by ray tracing through aspheric surfaces," The college of Optometrists, pp. 153-161, 2005, vol. 25.

Olsen T., et al., "Intraocular Lens Power Calculation with an Improved Anterior Chamber Depth Prediction Algorithm," Journal of Cataract & Refractive Surgery, 1995, vol. 21 (3), pp. 313-319.

Preussner et al., "Predicting postoperative intraocular lens position and refraction," J. Cataract Refractive Surgery, pp. 2077-2083, 2004, vol. 30.

Savini G., et al., "Intraocular Lens Power Calculation after Myopic Refractive Surgery: Theoretical Comparison of Different Methods," Ophthalmology, 2006, vol. 113 (8), pp. 1271-1282.

Wold S., et al., "The Co linearity Problem In Linear Regression, The Partial Least Squares (PLS) Approach To Generalized Inverses," Society for Industrial and Applied Mathematics Journal on Scientific and Statistical Computing, 1984, vol. 5 (3), pp. 735-743.

* cited by examiner

INTRAOCULAR LENSES WITH CUSTOMIZED ADD POWER

CROSS REFERENCES TO RELATED APPLICATIONS

This application is a divisional of and claims priority to U.S. patent application Ser. No. 16/128,231, filed Sep. 11, 2018, which claims the benefit under 35 U.S.C. § 119(e) of U.S. Provisional Patent Application No. 62/556,752, filed Sep. 11, 2017, all of which are incorporated herein by reference in their entirety.

BACKGROUND

Field

This disclosure generally relates to lenses with optical add power.

Description of Related Art

Patients suffering from presbyopia can benefit from multifocal lenses that are configured to provide distance vision correction as well as intermediate and/or near vision correction. Current multifocal intraocular lenses are offered in discrete add powers, that are fixed across the complete spherical equivalent power range.

SUMMARY

The systems, methods and devices of the disclosure each have several innovative aspects, no single one of which is solely responsible for the desirable attributes disclosed herein.

Presbyopic patients can benefit from multifocal lenses that can provide vision correction for distance and near and/or intermediate vision. Various embodiments of intraocular lenses (IOLs) contemplated in this application are configured to provide a spherical equivalent power for distance vision correction and an add power for near and/or intermediate vision correction. The add power can be customized based on a patient's ocular biometry and/or preferred reading distance.

An innovative aspect of this application is implemented in an intraocular lens for implantation in to the eye of a patient. The intraocular lens is a multifocal optic having a spherical equivalent optical power less than or equal to 50 Diopters and an optical add power customized for a patient's visual needs determined based on a position of the intraocular lens when implanted in the eye of the patient, and a parameter of the patient's eye. The position of the intraocular lens when implanted in the eye of the patient can be the effective lens position, the actual lens position or a combination thereof. The effective lens position can be calculated by Hoffer Q, Holladay I or Haigis formula. The actual lens position can be determined from a relationship between the anterior-chamber depth prior to the surgery and the actual IOL position measured from the anterior cornea after the surgery. The actual lens position can be determined from the vitreous length and the center thickness of the IOL. The optical add power can be customized based on at least one of: a corneal power, an axial length or an anterior chamber depth. The optical add power can be customized based on a preferred reading distance.

The optical add power for implementations of a multifocal lens optimized for viewing objects at a maximum distance of 50 cm and having a spherical equivalent optical power less than or equal to 10 Diopters can be between about 2.7 Diopter and about 3.4 Diopter.

The optical add power for implementations of a multifocal lens optimized for viewing objects at a maximum distance of 50 cm through the near vision zone and having a spherical equivalent optical power greater than 5 Diopter and less than or equal to 40 Diopters can be between about 2.5 Diopter and about 3.4 Diopter.

The optical add power for implementations of a multifocal lens optimized for viewing objects at a maximum distance of 42 cm and having a spherical equivalent optical power less than or equal to 10 Diopters can be between about 3.25 Diopter and about 4.0 Diopter, and The optical add power for implementations of a multifocal lens optimized for viewing objects at a maximum distance of 42 cm through the near vision zone and having a spherical equivalent optical power greater than 10 Diopter and less than or equal to 50 Diopters can be between about 3.0 Diopter and about 4.0 Diopter.

Another innovative aspect of this application is embodied in a kit comprising a plurality of intraocular lenses for implantation in to the eye of a patient. The kit comprises a plurality of multifocal optics having a spherical equivalent optical power less than or equal to 50 Diopters. Each of the plurality of multifocal optics comprise an optical add power that is optimized for viewing at one or more preferred near and/or intermediate distances. For each preferred distance, the plurality of multifocal optics have an optical add power in a first range for spherical equivalent optical powers less than or equal to 10 Diopters and an optical add power in a second non-overlapping range for spherical equivalent optical powers greater than 10 Diopter and less than or equal to 50 Diopters. The first range can be between 2.75 Diopter and 4.0 Diopter. The second range can be between 2.25 Diopter and 2.75 Diopter. The preferred distance can be 50 cm or 42 cm. The optical add power of the plurality of multifocal optics optimized for each preferred distance can be calculated using a formula that depends on a position of the intraocular lens when implanted in the eye of the patient, a shape of the patient's eye, and the preferred reading distance.

Another innovative aspect of this application contemplates a method of manufacturing an intraocular lens, the method comprising manufacturing an intraocular lens having a spherical equivalent power and a customized optical add power, wherein the customized optical add power is based on at least one of an ocular biometry of an individual, a position of the intraocular lens in the eye, or a preferred reading distance, and wherein ocular biometry comprises at least one of an axial length (AL) of the individual's eye, corneal power (K) or anterior chamber depth.

Another innovative aspect of this application contemplates a method of designing and manufacturing a multifocal IOL that is customized for a particular reading distance, wherein the add power differs depending on the base power Yet another innovative aspect of this application contemplates a method of selecting the add power of an intraocular lens, the method comprising determining a customized optical add power based on at least one of an ocular biometry of an individual, a position of the intraocular lens in the eye, or a preferred reading distance, and selecting from a range of existing IOLs an IOL that has an optical add power closest to the determined customized optical add power and a spherical equivalent power closest to a desired spherical equivalent power, wherein ocular biometry comprises at least one of an axial length (AL) of the individual's eye, corneal power (K) or anterior chamber depth.

BRIEF DESCRIPTION OF THE DRAWINGS

The systems, methods and devices may be better understood from the following detailed description when read in conjunction with the accompanying schematic drawings, which are for illustrative purposes only. The drawings include the following figures.

DETAILED DESCRIPTION

Figure 1:
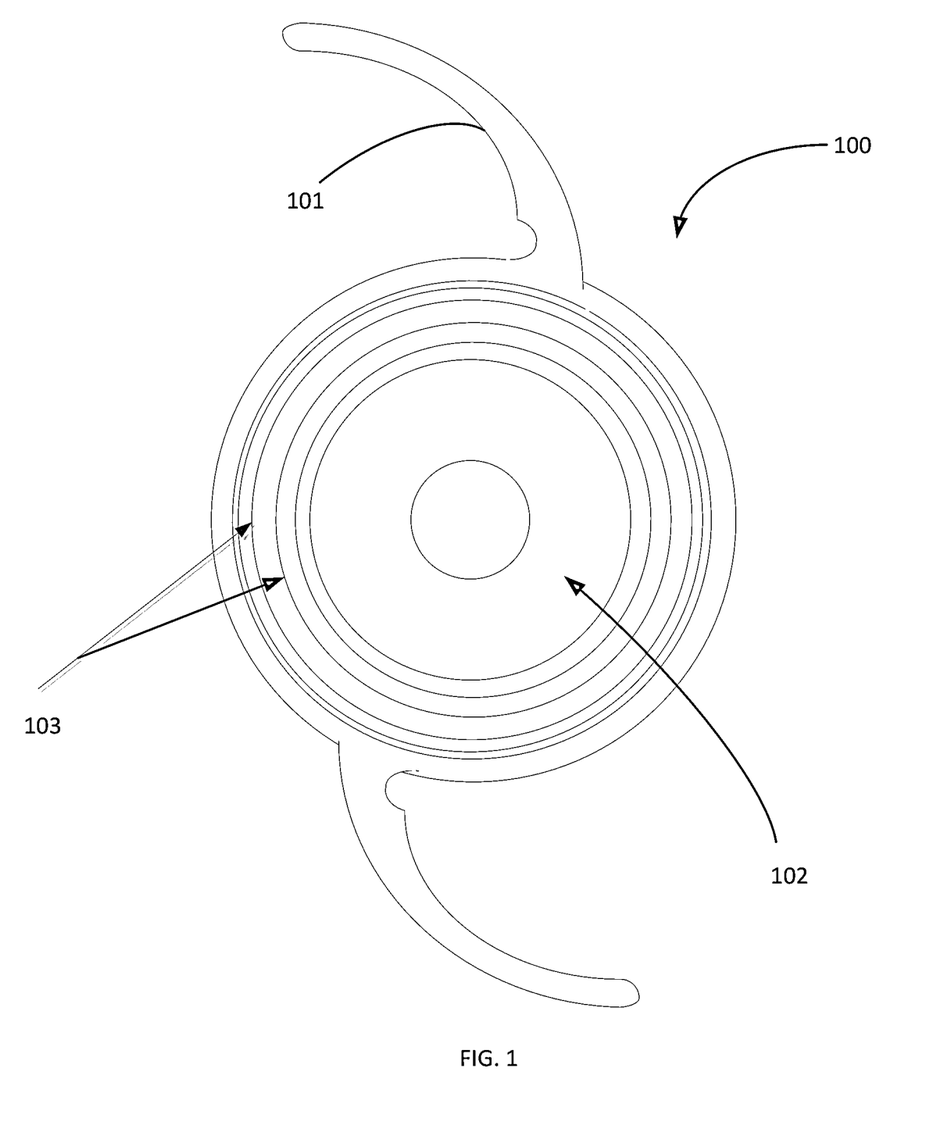
FIG. 1 illustrates an embodiment of a multifocal intraocular lens.

Presbyopic patients can benefit from multifocal lenses that can provide vision correction for distance and near and/or intermediate vision. FIG. 1 illustrates an embodiment of a multifocal intraocular lens 100 comprising an optic 102 and a haptic 101. The optic 102 comprises a plurality of optical zones 103 that are configured to focus light from different distances onto the retina. The plurality of optical zones 103 can comprise diffractive and/or refractive features that are configured to focus light from different distances onto the retina.

Current multifocal intraocular lenses (IOLs) are offered in discrete add powers. The discrete add powers are fixed (or constant) across the entire range of spherical equivalent powers provided by the IOL. For example, different IOLs configured to provide different spherical equivalent power are configured to provide a fixed add power (e.g., 4.0 Diopter, 2.75 Diopter, or 3.25 Diopter). The effect of the fixed add power can be determined by transforming an add power in the IOL plane to an add power in the spectacle plane using a fixed ratio. As used herein spherical equivalent power can refer to the base optical power of the IOL that provides distance vision correction. The spherical equivalent power can also be referred to as the IOL power. The spherical equivalent power can vary between −10 Diopter and 50 Diopter. For example, the spherical equivalent power can between 0 Diopter and 40 Diopter, or between 5 Diopter and 34 Diopter.

One study indicates that the near focal distance of an eye implanted with a multifocal intraocular lens can depend on an effective lens position (ELP) of the multifocal intraocular lens in the eye. The ELP can depend on a variety of parameters including but not limited to axial length, corneal power and, preoperative anterior chamber depth or a combination thereof. Another study indicates that the optimum distance that provides an optimized near vision performance with a multifocal IOL that is configured to provide a fixed add power (e.g., 4.0 Diopter) can vary depending on the ocular biometry (e.g., axial length, or anterior chamber depth). For example, the optimum distance that provides an optimized near vision performance with a multifocal IOL having a fixed add power of 4.0 Diopter is about (i) 29.5 cm for patients with hyperopia, (ii) about 32.8 cm for emmetropes and (iii) about 34.5 cm for patients with myopia. Thus, according to this study, the dioptric power yielding the best near vision performance is substantially correlated with axial length and anterior chamber depth of the patient's eye. Accordingly, it may be advantageous to customize the add power of IOLs based on a patient's ocular biometry, the placement of the IOL when implanted and/or preferred reading distance. Ocular biometry can include a variety of ocular parameters including but not limited to axial length (AL) of the eye, corneal power (K), vitreous length and/or anterior chamber depth.

This application contemplates multifocal IOLs with optical add power that is customized for an individual patient. The customized optical add power can depend on various parameters including but not limited to the position of the IOL in the eye, axial length (AL) of the eye, corneal power (K), anterior chamber depth, or a combination thereof. The position of the IOL in the eye can correspond to the ELP or the actual lens position (ALP). The ELP can be calculated using the Holladay, Hoffer Q or Haigis formula The ALP can be determined in a variety of ways. For example, in one method, the ALP can be determined from a relationship between the anterior-chamber depth prior to the surgery and the actual IOL position measured from the anterior cornea also referred to as anterior chamber depth after the surgery. The relationship between the anterior-chamber depth prior to the surgery and the anterior chamber depth after the surgery can be linear. The anterior-chamber depth prior to the surgery can be measured with anterior segment slit-lamp images. The anterior chamber depth after the surgery can be measured with an anterior chamber OCT instrument. As another example, in another method, the ALP can be determined based on the post-operative vitreous length and the center thickness of the implanted IOL.

The ELP can be determined from various IOL power calculation formulae that are used currently. For example, ELP can be determined using the formulae and methods described in the articles from Holladay, Hoffer and Haigis mentioned above. However, this application also contemplates the determination of the ELP based on customized methods. Any combination of ELP and ALP determination methods can be used to optimize the optical add power that optimizes individual's near vision performance. The customized add power can be calculated using the principles of paraxial optics to determine the relationship between add power, ocular biometry and distance that provides the best near and/intermediate vision performance.

For example, the customized optical add power in Diopters of a multifocal IOL for an individual can be calculated using equation 1 below:

$$\text{Add power} = \tag{1}$$

-continued $$\frac{1.336}{\frac{1.336}{K} - \frac{IOL\ position}{1000}} - \frac{1.336}{K - 100 \Big/ \frac{reading\ distance}{[1 - 100/reading\ distance] * 0.012}} - \frac{IOL\ position}{1000}$$

Figure 2:
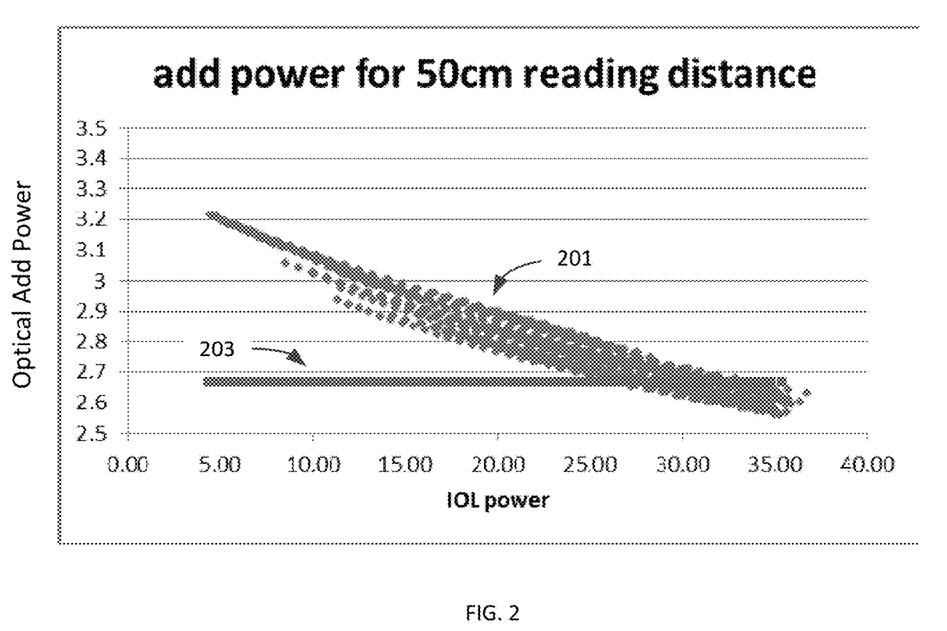
FIGS. 2-6 are graphs of customized optical add power for different reading distance versus spherical equivalent power.

In equation (1) above, IOL position corresponds to ELP or ALP in millimeters (mm) determined from any of the equations or methods described herein, K corresponds to the corneal power in Diopters, reading distance corresponds to the distance for best near vision performance in centimeters (cm). The optical add power can be calculated independently from the calculation of the spherical equivalent power of the IOL. In contrast to current multifocal IOLs that are available, the customized optical add power of various embodiments of multifocal IOLs contemplated by this application is not constant for different spherical equivalent power. Instead, the customized optical add power can vary based on the spherical equivalent power of the IOL as discussed below with reference to FIGS. 2-6 which illustrate graphs of customized optical add power for different reading distance versus spherical equivalent power. A wide range of ocular biometries based on biometry data sets that were previously analyzed were used to study the relation between add power and reading distance given by equation (1) above for the ELP calculated by any of the various methods described herein. To study the relation between add power and reading distance different biometry combinations were created with corneal power in a range between 38D to 45D, axial length in a range between 20 mm to 30 mm and anterior chamber depth in a range between 2 mm to 4 mm FIG. 2 shows the variation of the customized optical add power as calculated by equation (1) represented by curve 201 with respect to spherical equivalent power (also referred to as IOL power) for a reading distance of 50 cm. For each biometry combination, the ELP was calculated according to the Haigis formula. This value was used for IOL position in equation (1) to calculate customized optical add power represented by curve 201. The line 203 corresponds to a fixed optical add power of about 2.7 Diopters in the IOL plane which was calculated by translating the optical add power calculated in the spectacle plane for a reading distance of 50 cm to the IOL plane by assuming a fixed ratio of 0.75. This method of calculating the optical add power represents the current state of the art to relate optical add power to reading distance. It is observed from FIG. 2 that optical add power varies inversely to spherical equivalent power. Accordingly, optical add power is higher for lower spherical equivalent power. It is further observed from FIG. 2 that the current state of the art underestimates the optical add power for eyes that require lower spherical equivalent power, such as, for example, patients who have axial length longer than a normal average human eye, who are typically myopic prior the cataract surgery. Some average human eyes can also require lower spherical equivalent power and the current state of the art can underestimate the required optical add power.

Figure 3:
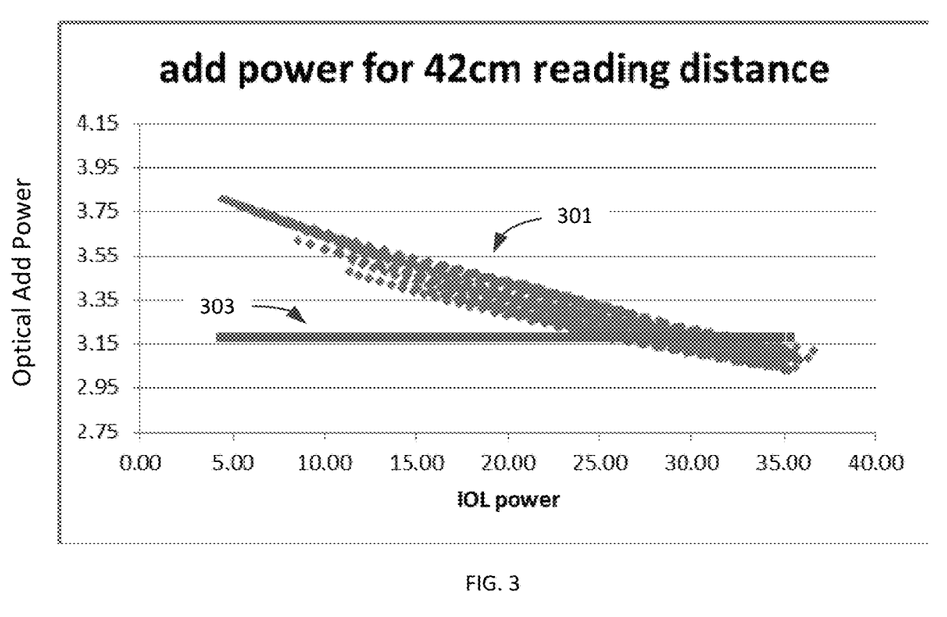
Figure 4:
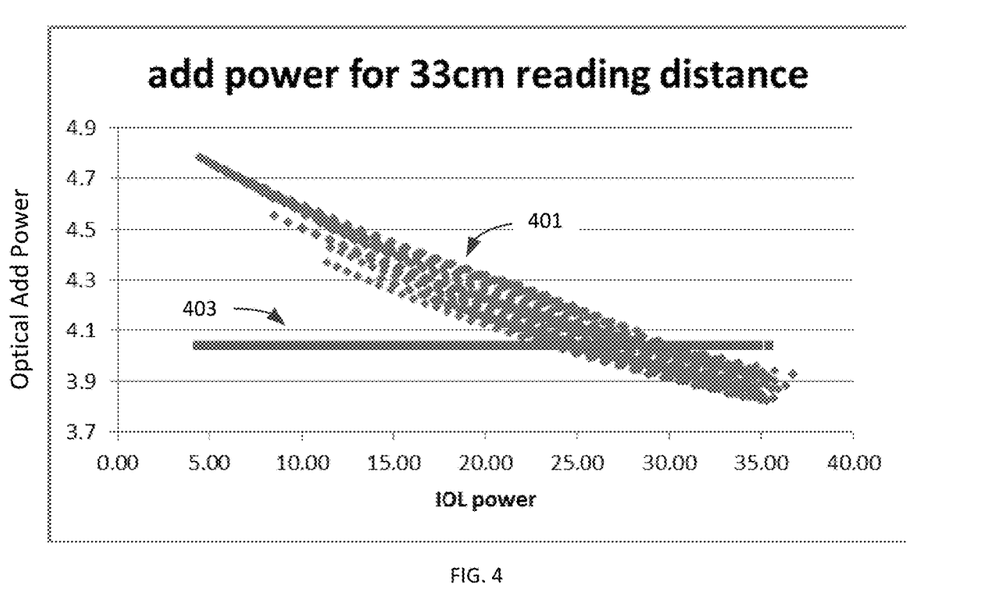

FIG. 3 illustrates the variation of the customized optical add power as calculated by equation (1) represented by curve 301 with respect to spherical equivalent power (also referred to as IOL power) for a reading distance of 42 cm. The line 303 corresponds to a fixed optical add power of about 3.15 Diopters which was calculated by translating the optical add power calculated in the spectacle plane for a reading distance of 42 cm to the IOL plane by assuming a fixed ratio of 0.75 in accordance with the current state of the art. FIG. 4 illustrates the variation of the customized optical add power as calculated by equation (1) represented by curve 401 with respect to spherical equivalent power (also referred to as IOL power) for a reading distance of 33 cm. The line 403 corresponds to a fixed optical add power of about 4.1 Diopters which was calculated by translating the optical add power calculated in the spectacle plane for a reading distance of 33 cm to the IOL plane by assuming a fixed ratio of 0.75 in accordance with the current state of the art. The customized optical add power in FIGS. 3 and 4 were calculated using equation (1) and the ELP per Haigis formula. As discussed above with reference to FIG. 2, the customized optical add power varies inversely with respect to the spherical equivalent power in FIGS. 3 and 4.

Figure 5:
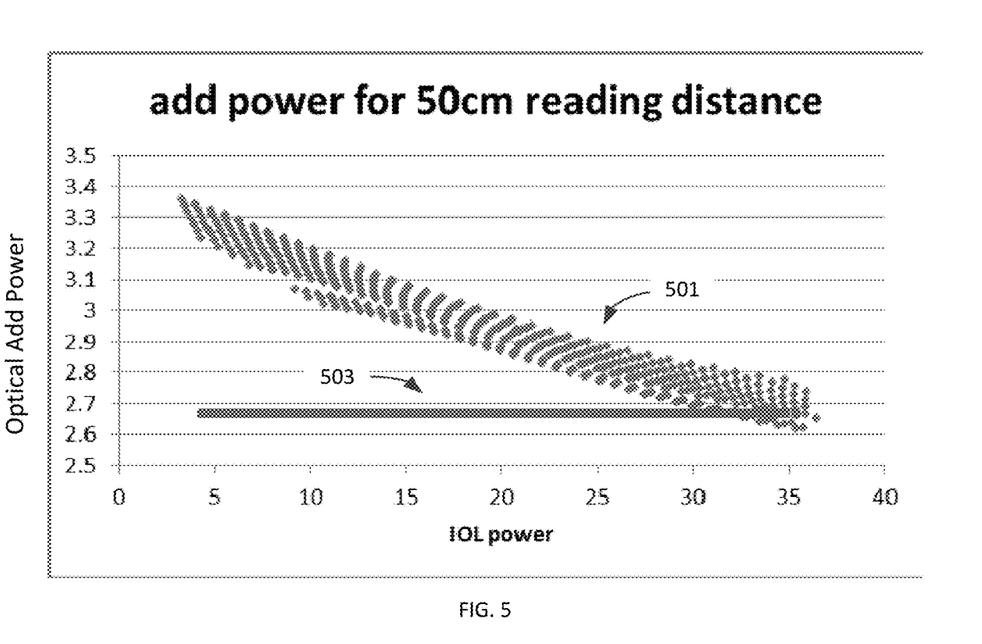

The IOL position can be calculated using other formulae and/or methods described herein. For example, the IOL position in equation (1) can correspond to the ELP calculated in accordance with the Hoffer Q formula. Curve 501 of FIG. 5 represents the customized optical add power as calculated by equation (1) for a reading distance of 50 cm, wherein the IOL position in equation (1) corresponds to the ELP calculated in accordance with the Hoffer Q formula. Curve 503 of FIG. 5 corresponds to the fixed optical add power for a reading distance of 50 cm calculated in accordance with the current state of art. It is observed from FIG. 5 that customized optical add power obtained using ELP calculated in accordance with the Hoffer Q formula varies inversely with respect to the spherical equivalent power.

Figure 6:
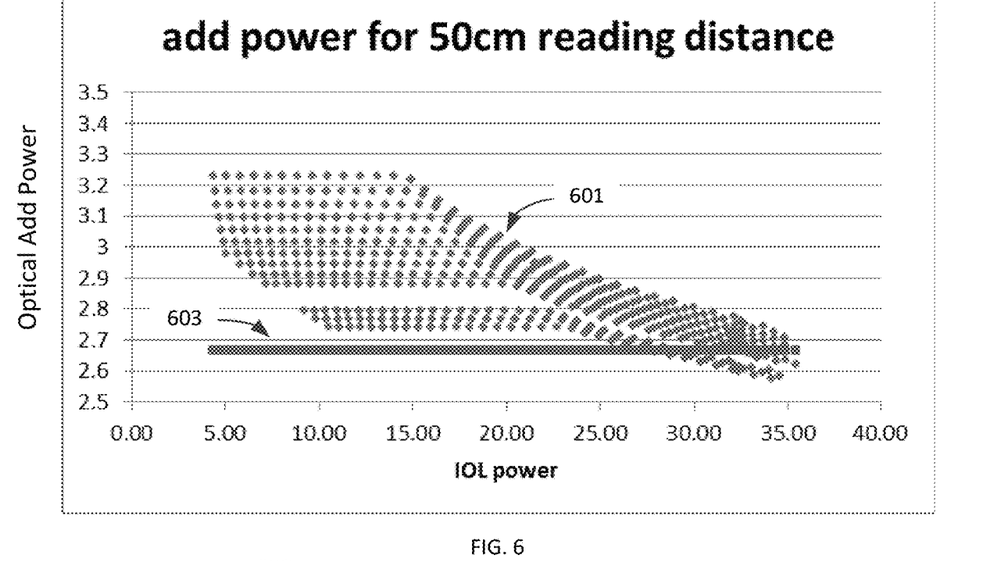

FIG. 6 illustrates the variation of the customized optical add power (represented by curve 601) as calculated by equation (1) for a reading distance of 50 cm, wherein the IOL position in equation (1) corresponds to the ELP calculated in accordance with the Holladay I formula with respect to the spherical equivalent power. It is observed from FIG. 6 that the optical add power varies for different biometry configurations. When the Holladay I formula is used to determine the ELP, the variation of the optical add power with IOL power is different from the variation of the optical add power with IOL power when the ELP is determined using Hoffer Q or Haigis formulae.

Figure 7:
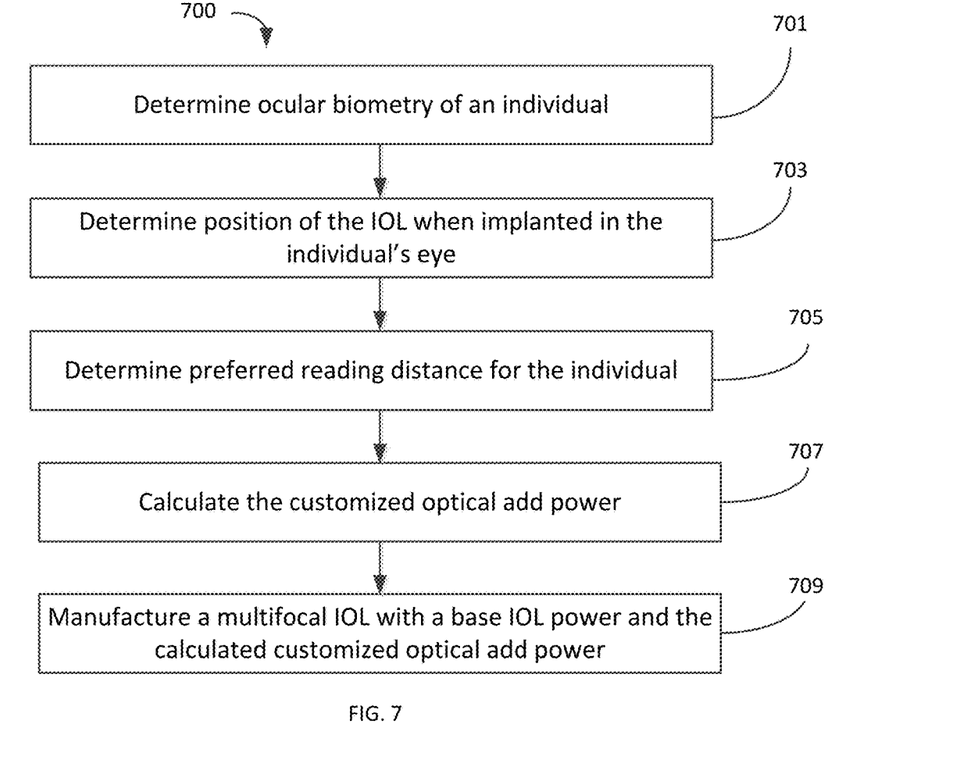
FIG. 7 is a flow chart of an example method of manufacturing a multifocal IOL having a base IOL power and a customized optical add power.

One or more multifocal IOLs having a base IOL power (also referred to as spherical equivalent power) and a customized optical add power can be manufactured using a variety of IOL manufacturing methods. FIG. 7 is a flowchart illustrating an example method of manufacturing. The method comprises determining ocular biometry of an individual as shown in block 701. The method further comprises determining the position of the IOL when implanted in the individual's eye as shown in block 703. The position of the IOL when implanted in the eye can be calculated using any of the methods described herein and it can be either the actual lens positon (ALP), the effective lens positon (ELP) or a combination of these. The method further comprises determining a preferred reading distance for the individual as shown in block 705. The determination of the ocular biometry, position of the IOL when implanted in the individual's eye and the preferred reading distance need not be performed in the order illustrated in FIG. 7. In various cases, the determination of the ocular biometry, position of the IOL when implanted in the individual's eye and the preferred reading distance can be performed in a different order or simultaneously. The method further comprises calculating a customized optical add power for the individual based on the determined ocular biometry, position of the IOL when implanted in the individual's eye and the preferred reading distance as shown in block 707. The calculation can be performed using a formula, such as, for example, the formula of equation (1).

Figure 8:
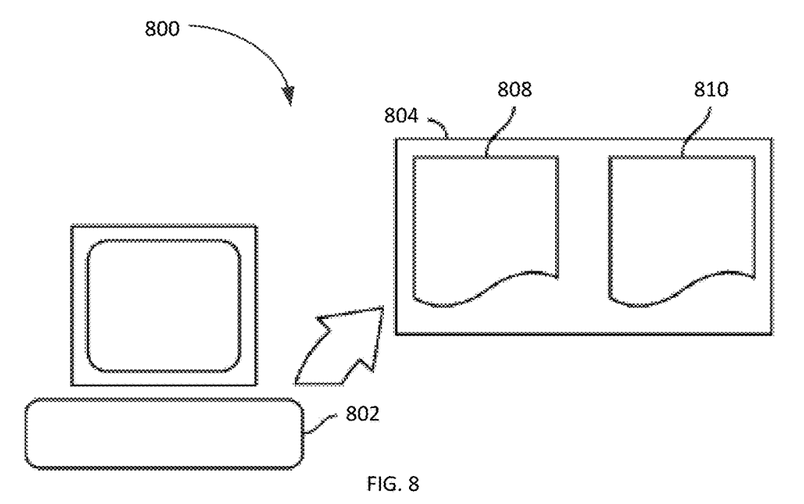
FIG. 8 is a graphical representation of the elements of a computing system used to calculate a customized optical add power.

An electronic processing system configured to execute instruction stored in a non-transitory computer storage medium can be employed to calculate the optimized optical add power. FIG. 8 illustrates an example of an electronic processing system 800 that can be used to calculate the customized optical add power. The electronic processing system 800 comprises an electronic hardware processor 802 and a computer readable memory 804 coupled to the electronic hardware processor 802. The computer readable memory 804 has stored therein an array of ordered values 808 and sequences of instructions 810 which, when executed by the electronic hardware processor 802, cause the electronic hardware processor 802 to perform certain functions or execute certain modules. For example, a module to calculate the customized optical add power can be executed. The electronic hardware processor 802 can be configured to receive the determined ocular biometry, position of the IOL when implanted in the individual's eye and the preferred reading distance electronically. In some embodiments, various ophthalmic instruments that are used to determine ocular biometry and the preferred reading distance can be in electronic communication with the electronic hardware processor 802.

The array of ordered values 808 may comprise, for example, one or more ocular dimensions of one or more human eyes, a desired refractive outcome, parameters of an eye model based on one or more characteristics of at least one eye, and data related to an IOL or set of IOLs such as a power, an aspheric profile, and/or a lens plane. In some embodiments, the sequence of instructions 810 includes determining the position of an IOL when implanted in the individual's eye and performing one or more calculations to determine a base IOL power and/or a customized optical add power that provides optimal near and/or intermediate and distance vision correction. The optimal near and/or intermediate and distance vision correction can be based on equation 1. In some embodiments, the sequence of instruction 810 can be configured to iteratively optimize various parameters of the IOL including but not limited to base IOL power and the customized optical add power to optimize near and/or intermediate and distance vision correction. The system can also be programmed so that it accepts postoperative outcomes. For any given reading distance, as well as the postoperative IOL position and biometry, the system can be configured to calculate the optical add power that is customized to the patient. The calculation can be performed in an iterative fashion, so that the system can adjust an algorithm used to calculate the optical add power to improve accuracy for a wide range of optical biometries.

The electronic processing system 800 may be a general purpose desktop or laptop computer or may comprise hardware specifically configured performing the desired calculations. In some embodiments, the electronic processing system 800 is configured to be electronically coupled to another device such as a phacoemulsification console or one or more instruments for obtaining measurements of an eye or a plurality of eyes. In other embodiments, the electronic processing system 800 is a handheld device that may be adapted to be electronically coupled to one of the devices just listed. In yet other embodiments, the electronic processing system 800 is, or is part of, refractive planner configured to provide one or more suitable intraocular lenses for implantation based on physical, structural, and/or geometric characteristics of an eye, and based on other characteristics of a patient or patient history, such as the age of a patient, medical history, history of ocular procedures, life preferences, and the like.

Generally, the instructions of the electronic processing system 800 will include elements of the method 700 and/or parameters and routines for performing calculations based on one or more formulae to determine at least one of a position of the IOL when implanted in the eye, customized optical add power, base IOL power or higher order aberration corrections.

In certain embodiments, the electronic processing system 800 includes or is part a phacoemulsification system, laser treatment system, optical diagnostic instrument (e.g., autorefractor, aberrometer, and/or corneal topographer, or the like). For example, the computer readable memory 804 may additionally contain instructions for controlling the handpiece of a phacoemulsification system or similar surgical system. Additionally or alternatively, the computer readable memory 804 may additionally contain instructions for controlling or exchanging data with an autorefractor, aberrometer, tomographer, and/or topographer, or the like.

In some embodiments, the electronic processing system 800 includes or is part of a refractive planner. The refractive planner may be a system for determining one or more treatment options for a subject based on such parameters as patient age, family history, vision preferences (e.g., near, intermediate, distant vision), activity type/level, past surgical procedures.

This application also contemplates manufacturing An IOL kit comprising at least two multifocal IOLs, each having a base IOL power and a customized add power. The customized add power can be determined based on an individual's near and or intermediate vision requirements (e.g., a preferred reading distance), the individual's ocular biometry and/or the position of the IOL when implanted in the eye as discussed herein. The at least two multifocal IOLs can be manufactured according to the various manufacturing methods described herein.

Figure 9:
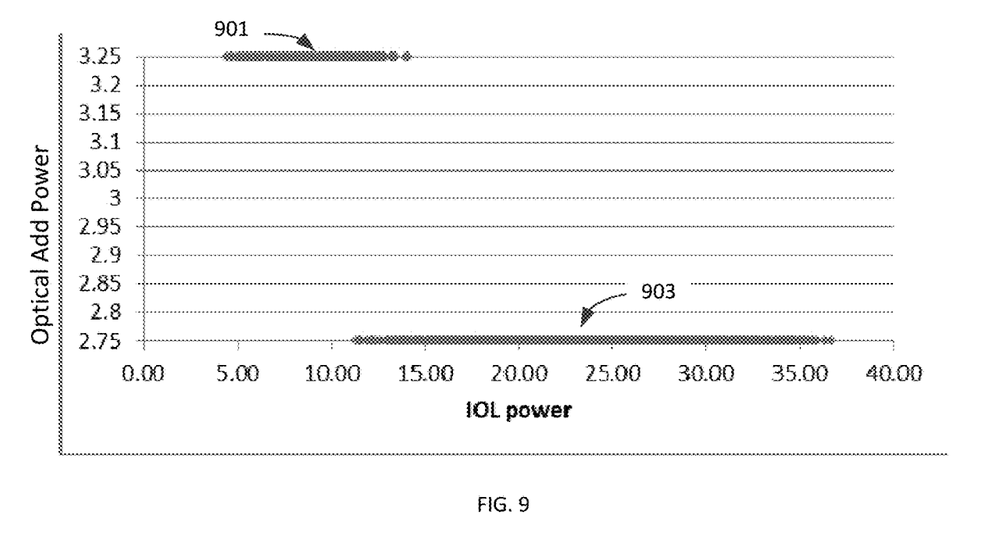
FIG. 9 illustrates a graph of optical add power for a multifocal IOL for different spherical equivalent powers.

FIG. 9 illustrates the selection of the add power from customized calculations for a standard multifocal IOL (e.g., TECNIS® multifocal IOL) for various base IOL powers. The standard multifocal IOL can have different fixed optical add powers (e.g., 2.75D, 3.25D and 4.00D in the IOL plane). The customized optical add power was calculated using equation (1) above, wherein the IOL position corresponds to ELP determined using the Haigis formula for a preferred reading distance of 50 cm for a wide range of ocular biometries. These configurations were the same as used in the examples above. As noted from FIG. 9, the selection of the add power for a particular reading distance (i.e. 50 cm) varies depending on the IOL power. For base IOL powers less than or equal to about 10 Diopters the add power closer to the custom add power for a 50 cm reading distance has a first value of about 3.25 Diopters. For a base power greater than 15D, the add power closer to the custom add power fora 50 cm reading distance has a second value of ab out 2.75 Diopters. For base powers between 10D and 15D the add power closer to the custom add power varies between 2.75D and 3.25D, depending on particular eye's biometry.

For other embodiments of IOLs, the selection of the add power from customized optical add power for base IOL powers less than or equal to a threshold optical power can be in a first range and the customized optical add power for base IOL powers greater than or equal to the threshold optical power can be in a second range. The threshold optical power can be greater than or equal to about 10 Diopters, greater than or equal to about 12.5 Diopters, greater than or equal to about 15 Diopters, less than or equal to about 20 Diopters, less than or equal to about 25 Diopters, or any value in a range/sub-range defined by these values. Furthermore, different thresholds can be defined depending on the available add power steps.

The first range and the second range of optical add power can be non-overlapping. In various embodiments, the first range of optical add powers can be greater than or equal to about 2.9 Diopters and less than or equal to ab out 5.0 Diopters, such as for example, greater than or equal to about 3.0 Diopters and less than or equal to about 4.5 Diopters, greater than or equal to about 3.0 Diopters and less than or equal to about 4.25 Diopters, greater than or equal to about 3.0 Diopters and less than or equal to about 4.0 Diopters, greater than or equal to about 3.0 Diopters and less than or equal to about 3.75 Diopters, greater than or equal to about 3.0 Diopters and less than or equal to about 3.50 Diopters, greater than or equal to about 3.0 Diopters and less than or equal to about 3.25, greater than or equal to about 3.25 Diopters and less than or equal to about 4.5 Diopters, greater than or equal to about 3.25 Diopters and less than or equal to about 4.25 Diopters, greater than or equal to about 3.25 Diopters and less than or equal to about 4.0 Diopters, greater than or equal to about 3.25 Diopters and less than or equal to about 3.75 Diopters, greater than or equal to about 3.25 Diopters and less than or equal to about 3.50, greater than or equal to about 3.50 Diopters and less than or equal to about 4.5 Diopters, greater than or equal to about 3.50 Diopters and less than or equal to about 4.25 Diopters, greater than or equal to about 3.50 Diopters and less than or equal to about 4.0 Diopters, greater than or equal to about 3.50 Diopters and less than or equal to about 3.75 Diopters, greater than or equal to about 3.75 Diopters and less than or equal to about 4.5 Diopters, greater than or equal to about 3.75 Diopters and less than or equal to about 4.25 Diopters, greater than or equal to about 3.75 Diopters and less than or equal to about 4.0 Diopters, greater than or equal to about 4.0 Diopters and less than or equal to about 4.5 Diopters, greater than or equal to about 4.0 Diopters and less than or equal to about 4.25 Diopters, greater than or equal to about 4.25 Diopters and less than or equal to about 4.5 Diopters, Diopters, or any value in a range/sub-range defined by these values.

In various embodiments, the first range of optical add powers can be greater than or equal to about 1.5 Diopters and less than or equal to about 3.25 Diopters, such as for example, greater than or equal to about 1.5 Diopters and less than or equal to about 3.00 Diopters, greater than or equal to about 1.5 Diopters and less than or equal to about 2.75 Diopters, greater than or equal to about 1.5 Diopters and less than or equal to about 2.5 Diopters, greater than or equal to about 1.5 Diopters and less than or equal to about 2.25 Diopters, greater than or equal to about 1.65 Diopters and less than or equal to about 3.25 Diopters, greater than or equal to about 1.65 Diopters and less than or equal to about 3.00 Diopters, greater than or equal to about 1.65 Diopters and less than or equal to about 2.75 Diopters, greater than or equal to about 1.65 Diopters and less than or equal to about 2.5 Diopters, greater than or equal to about 1.65 Diopters and less than or equal to about 2.25 Diopters, greater than or equal to about 1.75 Diopters and less than or equal to about 3.25 Diopters, greater than or equal to about 1.75 Diopters and less than or equal to about 3.00 Diopters, greater than or equal to about 1.75 Diopters and less than or equal to about 2.75 Diopters, greater than or equal to about 1.75 Diopters and less than or equal to about 2.5 Diopters, greater than or equal to about 1.75 Diopters and less than or equal to about 2.25 Diopters, greater than or equal to about 2.00 Diopters and less than or equal to about 3.25 Diopters, greater than or equal to about 2.00 Diopters and less than or equal to about 3.00 Diopters, greater than or equal to about 2.00 Diopters and less than or equal to about 2.75 Diopters, greater than or equal to about 2.00 Diopters and less than or equal to about 2.5 Diopters, greater than or equal to about 2.00 Diopters and less than or equal to about 2.25 Diopters, or any value in a range/sub-range defined by these values.

CONCLUSION

The systems and methods described herein can be used to design and manufacture multifocal IOLs that are customized to an individual's ocular biometrics, placement of the IOL in the individual's eye and the individual's near distance vision requirements (e.g., preferred reading distance, preferred reading position, length of arms, etc.). The add power of a multifocal IOL designed and manufactured according to the concepts discussed herein is optimized for an individual to view objects at a preferred distance in the near and/or intermediate vision zone. This is in contrast to existing multifocal IOLs that provide a fixed optical add power without taking into consideration an individual's ocular biometry and/or preferred reading distance.

The systems and methods described herein can be used to design and manufacture multifocal IOLs that are customized for a particular reading distance, wherein the add power differs depending on the base power. In that way, the spherical equivalent IOL power range can be designed and manufactured to provide with a particular reading distance instead of with a particular add power in the IOL plane.

The systems and methods described herein can be used to predict the optical performance of one or more lenses or lens models for a determined ocular biometry and a preferred reading distance. This can be advantageous to select one of a plurality of multifocal IOLs from an IOL kit that would optimize both near and/or intermediate and distance vision for an individual. For example, the optimum reading distance can be determined using a modified version of equation (1) from a known optical add power, ocular biometry of an individual and the position of the IOL in the eye. Thus, it is possible to predict the reading distance at which a multifocal IOL with a known optical add power would provide the best near vision performance for an individual.

The systems and methods described herein can be used to calculate the add power of a particular add on lens, sulcus lens, phakic lens, contact lens or laser treatment. The systems and methods described herein can be used to customize monovision outcomes. For example, a combination of a base IOL power and a customized optical add power can be used to obtain a desired monovision outcome for near or intermediate vision. A combination of a base IOL power and optical zones that provide different customized optical add powers can be used to improve visual outcomes for different distances in far, intermediate and near vision zones. The systems and methods described herein can be used to design and manufacture toric lenses configured to provide astigmatism correction based on an individual's ocular biometry, position of the IOL in the eye. In some embodiments of such toric lenses, the toric power steps can depend on the base power.

The above presents a description of the best mode contemplated of carrying out the concepts disclosed herein, and of the manner and process of making and using it, in such full, clear, concise, and exact terms as to enable any person skilled in the art to which it pertains to make and use the concepts described herein. The systems, methods and devices disclosed herein are, however, susceptible to modifications and alternate constructions from that discussed above which are fully equivalent. Consequently, it is not the intention to limit the scope of this disclosure to the particular embodiments disclosed. On the contrary, the intention is to cover modifications and alternate constructions coming within the spirit and scope of the present disclosure as generally expressed by the following claims, which particularly point out and distinctly claim the subject matter of the implementations described herein.

Although embodiments have been described and pictured in an example form with a certain degree of particularity, it should be understood that the present disclosure has been made by way of example, and that numerous changes in the details of construction and combination and arrangement of parts and steps may be made without departing from the spirit and scope of the disclosure as set forth in the claims hereinafter.

As used herein, the term "processor" refers broadly to any suitable device, logical block, module, circuit, or combination of elements for executing instructions. For example, the electronic hardware processor 802 can include any conventional general purpose single- or multi-chip microprocessor such as a Pentium® processor, a MIPS® processor, a Power PC® processor, AMD® processor, ARM processor, or an ALPHA® processor. In addition, the electronic hardware processor 802 can include any conventional special purpose microprocessor such as a digital signal processor. The various illustrative logical blocks, modules, and circuits described in connection with the embodiments disclosed herein can be implemented or performed with a general purpose processor, a digital signal processor (DSP), an application specific integrated circuit (ASIC), a field programmable gate array (FPGA), or other programmable logic device, discrete gate or transistor logic, discrete hardware components, or any combination thereof designed to perform the functions described herein. The electronic hardware processor 802 can be implemented as a combination of computing devices, e.g., a combination of a DSP and a microprocessor, a plurality of microprocessors, one or more microprocessors in conjunction with a DSP core, or any other such configuration.

Computer readable memory 804 can refer to electronic circuitry that allows information, typically computer or digital data, to be stored and retrieved. Computer readable memory 804 can refer to external devices or systems, for example, disk drives or solid state drives. Computer readable memory 804 can also refer to fast semiconductor storage (chips), for example, Random Access Memory (RAM) or various forms of Read Only Memory (ROM), which are directly connected to the communication bus or the electronic hardware processor 802. Other types of memory include bubble memory and core memory. Computer readable memory 804 can be physical hardware configured to store information in a non-transitory medium.

Methods and processes described herein may be embodied in, and partially or fully automated via, software code modules executed by one or more general and/or special purpose computers. The word "module" can refer to logic embodied in hardware and/or firmware, or to a collection of software instructions, possibly having entry and exit points, written in a programming language, such as, for example, C or C++. A software module may be compiled and linked into an executable program, installed in a dynamically linked library, or may be written in an interpreted programming language such as, for example, BASIC, Perl, or Python. It will be appreciated that software modules may be callable from other modules or from themselves, and/or may be invoked in response to detected events or interrupts. Software instructions may be embedded in firmware, such as an erasable programmable read-only memory (EPROM). It will be further appreciated that hardware modules may comprise connected logic units, such as gates and flip-flops, and/or may comprised programmable units, such as programmable gate arrays, application specific integrated circuits, and/or processors. The modules described herein can be implemented as software modules, but also may be represented in hardware and/or firmware. Moreover, although in some embodiments a module may be separately compiled, in other embodiments a module may represent a subset of instructions of a separately compiled program, and may not have an interface available to other logical program units.

In certain embodiments, code modules may be implemented and/or stored in any type of computer-readable medium or other computer storage device. In some systems, data (and/or metadata) input to the system, data generated by the system, and/or data used by the system can be stored in any type of computer data repository, such as a relational database and/or flat file system. Any of the systems, methods, and processes described herein may include an interface configured to permit interaction with users, operators, other systems, components, programs, and so forth.

What is claimed is:

1. A method of manufacturing a multifocal intraocular lens (IOL), the method comprising:
   manufacturing an intraocular lens having a spherical equivalent power and a customized optical add power, wherein the customized optical add power is based on an ocular biometry of an individual, a position of the intraocular lens in the eye, and a preferred reading distance,
   wherein ocular biometry comprises at least one of an axial length (AL) of the individual's eye, corneal power (K) or anterior chamber depth, and
   wherein for a preferred reading distance, the customized add power differs depending on the spherical equivalent power.

2. The method of claim 1, wherein the position of the intraocular lens in the eye is the actual lens position.

3. The method of claim 1, wherein the position of the intraocular lens in the eye is the effective lens position.

4. The method of claim 1, wherein the position of the intraocular lens in the eye is a combination of the actual lens position and the effective lens position.

* * * * *